(12) United States Patent
Lee et al.

(10) Patent No.: US 10,383,684 B2
(45) Date of Patent: Aug. 20, 2019

(54) PERICARDIAL ACCESS CATHETERS AND METHODS FOR USE

(71) Applicant: CLPH, LLC, Palo Alto, CA (US)

(72) Inventors: Randall J. Lee, Palo Alto, CA (US); Stephen A. Leeflang, Sunnyvale, CA (US); Christian S. Eversull, Palo Alto, CA (US)

( * ) Notice: Subject to any disclaimer, the term of this patent is extended or adjusted under 35 U.S.C. 154(b) by 0 days.

(21) Appl. No.: 15/057,027

(22) Filed: Feb. 29, 2016

(65) Prior Publication Data
US 2016/0249978 A1    Sep. 1, 2016

Related U.S. Application Data

(60) Provisional application No. 62/121,818, filed on Feb. 27, 2015.

(51) Int. Cl.
*A61B 1/05* (2006.01)
*A61B 18/14* (2006.01)
(Continued)

(52) U.S. Cl.
CPC ...... *A61B 18/1492* (2013.01); *A61B 1/00082* (2013.01); *A61B 1/05* (2013.01);
(Continued)

(58) Field of Classification Search
CPC .. A61N 2005/1003; A61B 2018/00577; A61B 18/1492; A61B 1/00082; A61B 5/6853; A61M 1/0023; A61M 1/008
See application file for complete search history.

(56) References Cited

U.S. PATENT DOCUMENTS

| 5,908,445 A * | 6/1999 | Whayne ............. A61B 1/00082 600/466 |
| 6,689,062 B1 * | 2/2004 | Mesallum ................ A61B 8/12 600/437 |
| 2001/0003798 A1 * | 6/2001 | McGovern ......... A61B 18/1485 606/41 |

(Continued)

OTHER PUBLICATIONS

Korean Intellectual Property Office, International Search Report for corresponding International Application No. PCT/US2016/019992, Form PCT/ISA/210, dated Jun. 22, 2016, 6 pages.
(Continued)

*Primary Examiner* — Christopher Koharski
*Assistant Examiner* — Natasha Patel
(74) *Attorney, Agent, or Firm* — William A. English; Vista IP Law Group LLP

(57) ABSTRACT

Apparatus and methods are provided for accessing a region within a patient's body and performing a procedure therein that includes a catheter including a tubular member comprising a proximal end, a distal end sized for introduction into a patient's body, an imaging assembly on the distal end, and a substantially transparent expandable member attached to the tubular member distal end such the imaging assembly is disposed within an interior of the expandable member, the imaging assembly imaging through a surface of the expandable member. The tubular member includes a drainage lumen communicating one or more drainage ports on the tubular member distal end proximal to the balloon for aspirating fluid from the patient's body. The catheter may be used to access a pericardial space and an ablation probe may be introduced through the catheter to treat heart tissue while fluid is infused and/or aspirated via the drainage ports.

25 Claims, 5 Drawing Sheets

(51) Int. Cl.
*A61B 5/00* (2006.01)
*A61M 1/00* (2006.01)
*A61M 25/06* (2006.01)
*A61B 1/00* (2006.01)
*A61B 1/313* (2006.01)
*A61B 1/06* (2006.01)
*A61B 5/042* (2006.01)
*A61B 18/00* (2006.01)

(52) U.S. Cl.
CPC .......... *A61B 1/0623* (2013.01); *A61B 1/0676* (2013.01); *A61B 1/3137* (2013.01); *A61B 5/0044* (2013.01); *A61B 5/0084* (2013.01); *A61B 5/6853* (2013.01); *A61M 1/008* (2013.01); *A61M 1/0023* (2013.01); *A61M 25/0662* (2013.01); *A61B 5/0422* (2013.01); *A61B 2018/0022* (2013.01); *A61B 2018/00285* (2013.01); *A61B 2018/00351* (2013.01); *A61B 2018/00577* (2013.01); *A61B 2018/00982* (2013.01); *A61B 2018/1467* (2013.01); *A61B 2218/002* (2013.01); *A61B 2218/007* (2013.01)

(56) References Cited

U.S. PATENT DOCUMENTS

| | | | |
|---|---|---|---|
| 2003/0199767 A1* | 10/2003 | Cespedes | A61B 5/01 600/473 |
| 2005/0197623 A1* | 9/2005 | Leeflang | A61M 25/0144 604/95.04 |
| 2005/0240147 A1* | 10/2005 | Makower | A61B 17/24 604/96.01 |
| 2008/0091104 A1* | 4/2008 | Abraham | A61B 8/0841 600/439 |
| 2009/0076498 A1* | 3/2009 | Saadat | A61B 18/1492 606/41 |
| 2009/0318797 A1* | 12/2009 | Hadani | A61B 1/00082 600/424 |
| 2010/0010488 A1* | 1/2010 | Kassab | A61B 18/1492 606/41 |
| 2010/0114093 A1 | 5/2010 | Mahapatra et al. | |

OTHER PUBLICATIONS

Korean Intellectual Property Office, Written Opinion for corresponding International Application No. PCT/US2016/019992, Form PCT/ISA/237, dated Jun. 21, 2016, 10 pages.

* cited by examiner

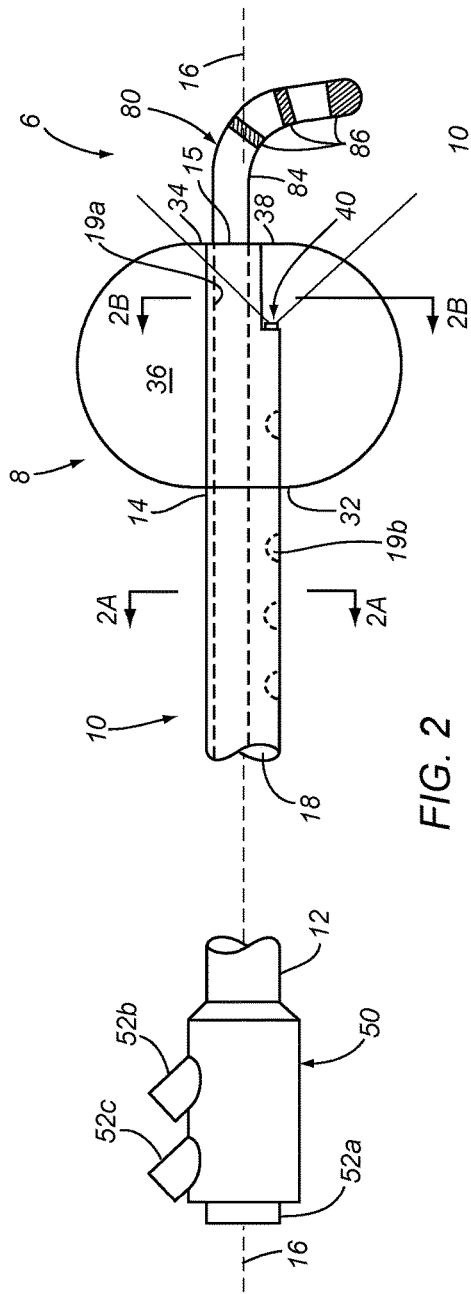
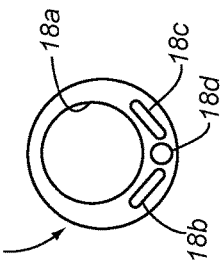
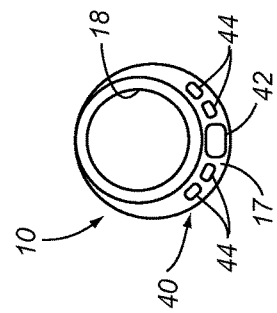
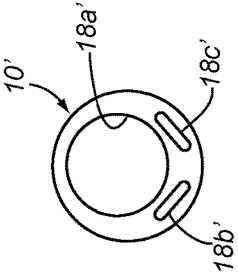
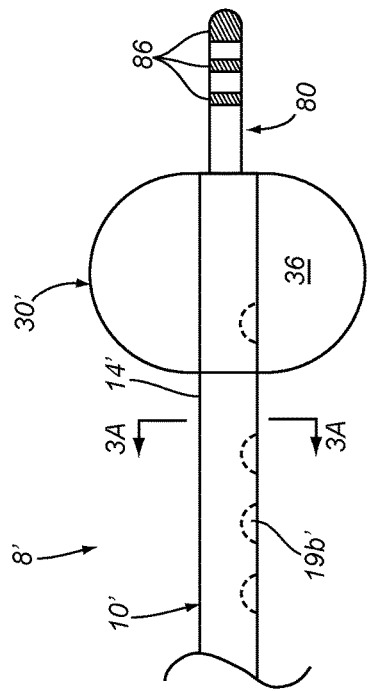

PERICARDIAL ACCESS CATHETERS AND METHODS FOR USE

RELATED APPLICATION DATA

The present application claims benefit of provisional application Ser. No. 62/121,818, filed Feb. 27, 2015, the entire disclosure of which is expressly incorporated by reference herein.

FIELD OF THE INVENTION

The present invention relates generally to catheters for accessing, imaging, and/or performing medical procedures within a patient's body, and more particularly to catheters for accessing a pericardial space of a patient's heart and to systems and methods for using such catheters, e.g., to drain fluid from the space while performing a procedure, such as an ablation procedure.

BACKGROUND

The pericardial space provides an advantageous approach for many medical procedures. For some procedures, an epicardial approach to the heart may provide more direct access with fewer risks, such as the risk of clotting or other embolic events (e.g., release of device debris, air, and the like), e.g., as compared to endovascular approaches. Recently, there has been a large increase in the number of therapies designed to access and treat the heart via an epicardial approach—both via a subxyphoid access as well as surgical access. Many of these treatments require careful positioning, e.g., to target specific areas as well as to avoid other specific areas. These areas can include atrial appendages, coronary arteries, coronary veins, fat pads, separate/individual chambers of the heart and/or walls thereof, and the like. These anatomies are difficult to visualize in general using standard imaging modalities, such as fluoroscopy or ultrasound, where resolution is poor and/or the ability to deliver and contain contrast is difficult, which may present a real and significant challenge to the development of truly therapeutic devices and procedures.

Likewise, fluid management in the pericardial space is critical to the overall success and safety of the procedure. Excess fluid in the pericardial space may compress the heart and reduce cardiac output. In the extreme, this may lead to cardiac tamponade. Furthermore, introduced fluid that is electrically insulating, e.g. air, can increase defibrillation thresholds, which can be dangerous in the event the patient develops a shockable arrhythmia during the procedure and requires cardioversion.

Therefore, apparatus and methods that facilitate medical procedures via epicardial approach would be useful.

SUMMARY

The present invention is directed to catheters for accessing, imaging, and/or performing medical procedures within a patient's body. More particularly, the present invention is directed to catheters for accessing a pericardial space of a patient's heart and to systems and methods for using such catheters, e.g., to drain fluid from the space while performing a procedure, such as an ablation procedure.

Various procedures may require introduction of fluid into the pericardial space. For example, RF ablation may be performed in conjunction with irrigation, e.g., to locally cool the tissue during energy delivery. Contrast media may be introduced into the pericardial space to enhance visualization. Air may be entrained into the pericardial space, for example, during device exchanges or around the access site as intra-thoracic pressure intermittently falls below atmospheric pressure. In all of these situations, systems and methods to control the accumulation and/or quickly remove fluid from the pericardial space would be advantageous.

In accordance with one embodiment, an apparatus is provided for accessing a region within a patient's body that includes a tubular member comprising a proximal end, a distal end sized for introduction into a patient's body, and one or more lumens extending between the proximal and distal ends; an imaging assembly on the distal end; and a substantially transparent expandable member attached to the tubular member distal end such the imaging assembly is disposed within an interior of the expandable member, the imaging assembly imaging through a surface of the expandable member, wherein the tubular member further comprises a drainage lumen extending from the tubular member proximal end to one or more drainage ports on the tubular member distal end proximal to the balloon. Optionally, a source of fluid and/or vacuum may be coupled to the tubular member proximal end and communicating with the drainage lumen for delivering and/or aspirating fluid via the one or more drainage ports.

In accordance with another embodiment, a system is provided for performing a procedure within a region of a patient's body that includes an access catheter comprising a tubular member including a proximal end, a distal end sized for introduction into a patient's body and carrying an imaging assembly within a balloon, an instrument lumen extending from the proximal end to an outlet in the distal end beyond the balloon, and a drainage lumen extending from the proximal end to one or more ports proximal to the balloon; an ablation probe comprising a proximal end, a distal end sized for introduction through the instrument lumen, and one or more ablation elements on the distal end for delivering energy to tissue; and a source of fluid coupled to one of the access catheter and the ablation probe for delivering fluid through a lumen to modulate energy delivered by the one or more ablation elements to tissue. In addition or alternatively, a source of vacuum may be coupled to the access catheter proximal and communicating with the drainage lumen for aspirating fluid from a region adjacent the access catheter distal end via the one or more ports.

In accordance with yet another embodiment, a method is provided for method is provided for performing procedure within a pericardial space adjacent a patient's heart and pericardium that includes introducing a distal end of a catheter into the pericardial space adjacent the patient's heart; expanding an expandable member on the distal end to separate the pericardium from the patient's heart; imaging tissue within the pericardial space to identify a target location of the patient's heart; introducing a medical device through the catheter and out the distal end; performing a procedure at the target location using the medical device; and draining fluid from the pericardial space via one or more drainage ports on the distal end of the catheter adjacent the expandable member.

In accordance with still another embodiment, a method is provided for performing procedure within a pericardial space adjacent a patient's heart and pericardium that includes introducing a distal end of a catheter into the pericardial space adjacent the patient's heart; expanding an expandable member on the distal end to separate the pericardium from the patient's heart; imaging tissue within the pericardial space to identify a target location of the patient's heart; introducing an ablation probe through the catheter and out the distal end; delivering energy from the ablation probe to tissue at the target location; delivering fluid into the pericardial space adjacent the target location to modulate delivering energy to the tissue; and draining fluid from the pericardial space via one or more drainage ports on the distal end of the catheter adjacent the expandable member.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 2 is a detail of an exemplary embodiment of a distal end of the catheter of FIG. 1.

FIGS. 2A and 2B are cross-sectional views of the distal end of the catheter of FIG. 2.

FIG. 3 is a detail of an alternative embodiment of a distal end of the catheter of FIG. 1.

FIG. 3A is a cross-sectional view of the distal end of the catheter of FIG. 2.

DETAILED DESCRIPTION OF THE EXEMPLARY EMBODIMENTS

Figure 1:
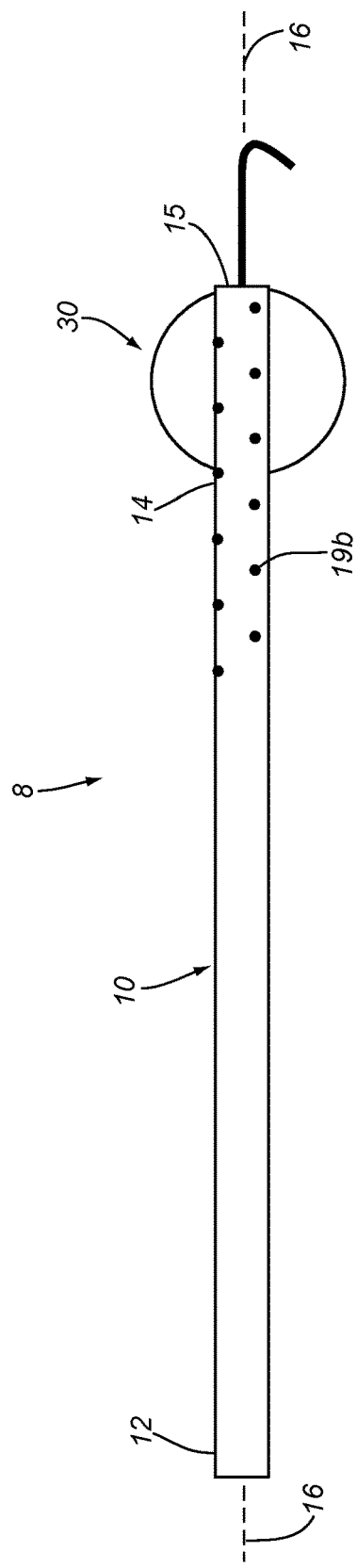
FIG. 1 is a side view of an exemplary embodiment of an access and/or drainage catheter for providing access into a patient's body.
Figure 6:
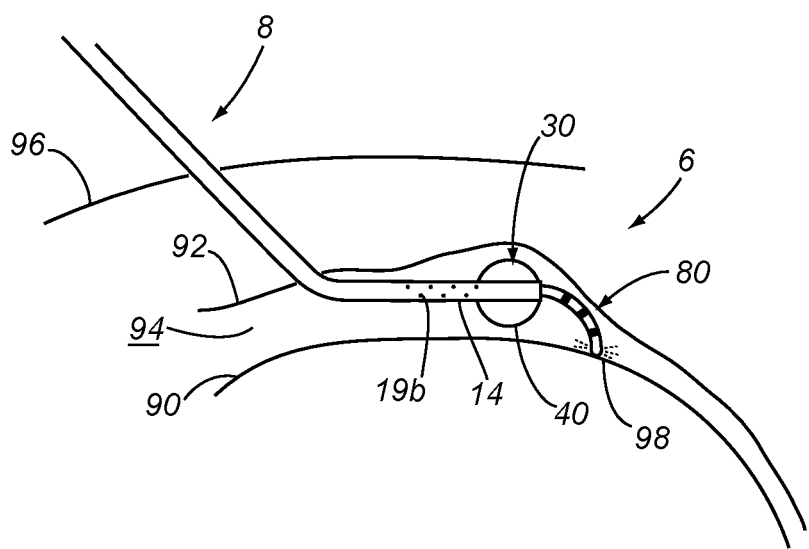
FIG. 6 is a cross-sectional view of a patient's body showing an exemplary method for using the catheter of FIG. 1 to introduce an ablation catheter into the pericardial space of the patient's heart.

Turning to the drawings, FIGS. 1 and 2 show an exemplary embodiment of an access sheath or catheter apparatus 8 for performing a medical procedure within a patient's body, e.g., for accessing a pericardial space adjacent a patient's heart, e.g., while draining fluid and/or imaging the heart. For example, the catheter 8 may be part of a system 6 for performing an ablation procedure on the patient's heart 90 using an ablation probe 80, e.g., as shown in FIG. 6. As best seen in FIG. 2, the catheter 8 generally includes an elongate tubular body or member 10 carrying a balloon 30 and an imaging assembly 40, and including one or more lumens, e.g., an instrument lumen 18a for introducing one or more devices into the patient's body, such as the ablation probe 80, and a drainage lumen 18b communicating with one or more drainage ports 19b adjacent the balloon 30. Optionally, the system 6 may include one or more additional components or devices, e.g., an access or delivery sheath, one or more stylets, and/or one or more guidewires or rails (all not shown).

Generally, as shown in FIG. 1, the catheter 8 includes an elongate tubular member 10 including a proximal portion or end 12, a distal portion or end 14 sized for introduction into a patient's body, a longitudinal axis 16 extending between the proximal and distal ends 12, 14, and one or more lumens 18 extending between the proximal and distal ends 12, 14. In exemplary embodiments, as shown in FIGS. 2 and 2A, the catheter 10 may include a primary or instrument lumen 18a that extend between the proximal and distal ends 12, 14, e.g., to an outlet 19a in a distal tip 15 of the tubular member 10, and one or more, relatively smaller, auxiliary lumens 18b-18d also extend at least partially between the proximal and distal ends 12, 14.

For example, the tubular member 10 may include one or more drainage lumens 18b (one shown) that extend from the proximal end 12 to one or more drainage ports 19b on the distal end 14, e.g., proximal to the balloon 30. As shown in FIG. 2, a plurality of drainage ports 19b are provided, which may be spaced apart axially relative to one another. In addition or alternatively, the drainage ports 19b may be spaced apart around the circumference of the distal end 14, e.g., as shown in FIG. 1. In this embodiment, multiple drainage lumens may be provided or internal passages (not shown) may be provided within the distal end 14 that communicate from a single drainage lumen 18b to the drainage ports 19b. Such a lumen and port(s) may allow infusion of saline or other transparent fluids to clear the field around the balloon 30 of blood or other obstructive materials and/or may allow aspiration to remove such materials, blood, contrast, saline, air, and/or other materials or fluids, e.g., that have accumulated in the pericardial space.

In addition, the tubular member 10 may include one or more inflation lumens 18c (one shown) that extend from the proximal end 12 and communicate with the interior 36 of the balloon 30, e.g., via an inflation port 37 on the distal end 14. The balloon 30 may be used in conjunction with imaging, e.g. to clear an optical path. Furthermore, the balloon 30 may be used to open the potential space around the heart, e.g., to provide separation between the heart surface and pericardial sac, e.g., to substantially isolate ablation on the surface of the heart and avoid damage to the pericardium. In addition, an imaging lumen 18b may extend between the proximal and distal ends 12, 14 for receiving one or more cables, wires, and the like (not shown) coupled to the imaging assembly 40

Optionally, the tubular body 10 may include one or more pull wires, e.g., if the distal end 14 of the catheter 10 is steerable and/or otherwise deflectable. For example, one or more additional lumens (not shown) may be provided that extend from the proximal end 12 to a desired location at the distal end 14 for receiving a pull wire or stylet (also not shown), which may be used to cause the distal end 14 to bend in a predetermined manner. In exemplary embodiments, one or more pull wires may be provided for directing the distal end 14 from a substantially straight to a curvilinear shape or a stylet may be inserted into the instrument lumen 18a to straighten or bend the distal end 14, as described elsewhere herein.

Optionally, the distal end 14 may include one or more features to enhance visibility under ultrasound, MRI or other imaging modalities, e.g., by providing one or more radiopaque markers on and/or doping one or more regions of the distal end 14 and/or the balloon 30, e.g. as known in the art.

The tubular member 10 may be substantially flexible, semi-rigid, and/or rigid along its length, and may be formed from a variety of materials, including plastic, metal, and/or composite materials, as is well known to those skilled in the art. For example, the catheter 10 may be substantially flexible at the distal end 14 to facilitate advancement through anatomy, and/or may be semi-rigid or rigid at the proximal end 12 to enhance pushability and/or torqueability of the catheter 8 without substantial risk of buckling or kinking. In an exemplary embodiment, the tubular member 10 may include an inner liner (not shown), e.g., at least partially or entirely surrounding or otherwise defining the instrument lumen 18a, a reinforcement layer surrounding the inner liner, and an outer jacket surrounding the reinforcement layer (all not shown for simplicity), each of which may extend at least partially between the proximal and distal ends 12, 14 of the tubular member 10. Optionally, the instrument lumen 18a and/or one or more of the auxiliary lumens 18b-18d may include lubricious material or may be formed from one or more layers of thermoplastic or other polymeric material including one or more coatings on the inner surface having desired properties, e.g., a hydrophilic and/or lubricious coating, e.g., similar to the liners disclosed in U.S. Pat. Nos. 7,550,053 and 7,553,387, and U.S. Publication No. 2009/0126862, the disclosures of which are expressly incorporated by reference herein.

Optionally, a distal portion of the catheter 8 may be pre-shaped, steerable or deflectable, i.e., may be bent, curved, or otherwise deflected. For example, the distal end 14 may be biased to a curved shape, e.g., having a predetermined radius of curvature. Optionally, a stylet (not shown) may be inserted into the tubular member 10 (e.g., into the instrument lumen 18a or a dedicated stylet lumen (not shown), e.g., to straighten the distal end 14 and/or otherwise support the distal end 14 during introduction into a patient's body. Alternatively, the catheter 10 may include one or more pull wires (not shown), which may be actuated to direct the distal end 14 between straightened and curved shapes, as desired, during use.

Returning to FIG. 2, a handle or hub 50 may be provided on the proximal end 12 of the tubular member 10, e.g., configured and/or sized for holding and/or manipulating the catheter 8 from the proximal end 12. In addition, the handle 50 may include one or more ports 52 communicating with respective lumens within the catheter 10. For example, port 52a may communicate with the instrument lumen 18a. Optionally, the port 52a include one or more valves, e.g., a hemostatic valve (also not shown), which may provide a substantially fluid-tight seal, while accommodating insertion of a device, such as ablation probe 80, into the instrument lumen 18a.

In addition, one or more side ports 52b, 52c may be provided, e.g., that communicate with the drainage lumen 18b and inflation lumen 18c, respectively. For example, a syringe or other source of inflation media (not shown) may be coupled to the side port 52c for introducing and/or removing fluid, e.g., saline, nitrogen, and the like, into and/or from the interior 36 of the balloon 30, e.g., to inflate and deflate the balloon 30. Similarly, a syringe, pump, or a vacuum line (not shown) may be coupled to the side port 52b, e.g., to selectively infuse fluid and/or aspirate material through the drainage ports 19b.

The handle 50 and/or proximal end 12 may also include one or more connectors, e.g., electrical connectors, and the like (not shown), for connecting the imaging assembly 40 to a controller, e.g., including a power source, processor, display, and the like (not shown), via one or more cables (also not shown).

Finally, the handle 50 may also include one or more actuators, such as sliders, buttons, switches, rotational actuators, locks, and the like, e.g., for activating and/or manipulating components on the distal end 14 or otherwise operating the apparatus 10. For example, one or more switches (not shown) may be provided on the controller and/or on the handle 50 for operating the imaging assembly 40. In addition, if the tubular member 10 is steerable or deflectable, one or more sliders or other actuators (not shown) may also be provided for directing respective pull wire(s) to deflect the distal end 14, or a port (not shown) may be provided for receiving a stylet, e.g., to straighten or otherwise deflect the distal end 14, as described elsewhere herein.

With particular reference to FIG. 2, the balloon 30 includes a proximal end 32 attached to the distal end 14 adjacent the drainage ports 19b and a distal end 34 attached to the distal end 24 distal to the proximal end 32, e.g., adjacent the distal tip 15. The proximal and distal ends 32, 34 of the balloon 30 may be secured to the outer surface of the tubular member 10, e.g., using an adhesive, heating, an interference fit, an outer collar (not shown), and the like. The balloon 30 may be expandable from a contracted or delivery condition (not shown) to an enlarged condition when fluid is introduced into an interior 36 of the balloon 30, e.g., as shown in FIGS. 1 and 2. Optionally, the balloon 30 may be shaped such that, in the enlarged condition, the balloon 30 may define a substantially flat distal surface, which may facilitate imaging tissue structures beyond the balloon 30 using the imaging assembly 40. Alternatively, the balloon 30 may have an ovular or elliptical or other cross-sectional shape when expanded, e.g., having a width substantially greater than its height in a plane transverse to the longitudinal axis 16 of the catheter 8, e.g., to provide rotational stability and/or bias as the catheter 8 tracks between the pericardial sac and the surface of the heart.

In an exemplary embodiment, the balloon 30 may be formed from compliant and/or elastic materials, e.g., elastomeric materials such as silicone, latex, isoprene, and chronoprene. The compliance of the balloon 30 may facilitate clearing fluid when the balloon 30 is pressed against or otherwise contacts tissue surfaces. Alternatively, the balloon 30 may be formed from substantially noncompliant material, e.g., polytetrafluoroethylene (PTFE), expanded polytetrafluoroethylene (EPTFE), fluorinated ethylenepropylene (FEP), polyethylene teraphathalate (PET), urethane, olefins, and polyethylene (PE), such that the balloon 30 expands to a predetermined shape when fully inflated to the enlarged configuration. The material may be sufficiently flexible and/or elastic such that the balloon 30 may conform substantially to the shape of contacted tissue structures, e.g., the epicardium of a patient's heart, which may displace blood or other fluid from between the balloon 30 and the contacted tissue to facilitate imaging through the balloon 30.

The material may also be substantially transparent, i.e., allow light from the imaging assembly 40 to pass therethrough and/or be reflected off tissue or other structures beyond the distal surface 38 of the balloon 30 back to the imaging assembly 40, as described elsewhere herein. As used herein, "transparent" refers to any material and/or fluid that may permit sufficient light to pass therethrough in order to identify or otherwise visualize objects through the material and/or fluid. "Light" as used herein may refer to light radiation within the visible spectrum, but may also include other spectra, such as infrared ("IR") or ultraviolet ("UV") light.

With additional reference to FIG. 2B, the imaging assembly 40 generally includes one or more cameras or other imaging element(s) 42 and one or more light sources 44, e.g., mounted on a distal imaging surface 17 of the tubular member 10. The imaging surface 17 may be offset proximally from the distal tip 15 of the tubular member 10 and the field of view of the imaging element(s) 42 may be oriented to image through the distal surface 38 of the balloon 30. As shown in FIG. 2, the imaging surface 17 is substantially perpendicular to the longitudinal axis 16 such that the field of view of the imaging element(s) 42 is oriented substantially distally and axially.

Optionally, the imaging surface may not be substantially perpendicular to the longitudinal axis 16 of the catheter 8, e.g., such that the field of view of the imaging element(s) 42 is angled relative to the distal end 14 of the tubular member 10, i.e., such that a center axis of the field of view defines an angle, e.g., an acute angle, relative to the longitudinal axis 16 of the catheter 8. Similarly, the illumination fields of the light sources 44 may also be angled relative to the distal end 14 of the tubular member 10, e.g., to enhance illuminating tissue structures offset from the distal end 14. The illumination fields of the light sources 44 may be substantially parallel to the field of view or may be offset relative to one another, if desired. In addition, the illumination fields may have a wider angle than the field of view, if desired, which may facilitate illumination and/or imaging of tissue and/or other features beyond the balloon 30.

In an exemplary embodiment, the imaging element 42 may include a CMOS (complementary metal-oxide-semiconductor) or CCD (charge-coupled device) sensor that is exposed within the interior 36 of the balloon 30 for capturing light images through the balloon 30. Alternatively, the imaging element 42 may include a bundle of optical fibers, e.g. a coherent image bundle, that extends between the proximal and distal ends 12, 14 of the catheter 10 and terminates adjacent the distal surface 15.

Optionally, one or more lenses, filters, and the like (not shown) may be coupled to the imaging element 42, e.g., to focus light from beyond the distal surface 38 of the balloon 30 onto the active area of the imaging element 42, direct a field of view of the imaging element 42, and/or filter undesired wavelengths of light, as known to those skilled in the art. Optionally, the imaging element 42 may be covered with a transparent protective coating, e.g., to prevent inflation media within the interior 36 from contacting the imaging element 42.

The one or more light sources 44 may include one or LEDs (light emitting diodes) and/or other light sources mounted on the distal surface 15 adjacent the imaging element 42, e.g., substantially surrounding the imaging element 42 to deliver light into the interior 36 and/or through the distal surface 38 of the balloon 30. Alternatively, one or more optical fibers may be provided that extend from the proximal end 12 of the catheter 10 to the distal surface 15, e.g., to emit light from a source in the controller.

The controller (not shown) may provide a power source for the imaging element 42 and/or light sources 44 and/or may receive image data from the imaging element 42. In addition, the controller may include one or more processors, displays or other output devices, memory, and the like (not shown) to process, display, and/or store the images acquired from the imaging element 42. For example, the imaging element 42 may acquire digital images and may convert the image data onboard to analog signals, which may be conveyed via the cables to the controller, which may convert the images back to digital images and/or further process the images for presentation on a display. Additional information on imaging assemblies and/or balloons that may be provided on the catheter 10 are disclosed in U.S. Pat. No. 6,979,290, the entire disclosure of which is expressly incorporated by reference herein.

Turning to FIGS. 3 and 3A, an alternative embodiment of a catheter 8' is shown that includes an elongate tubular member 10' carrying a balloon 30', generally similar to the catheter 8 except that the imaging assembly has been omitted. Similar to the catheter 8, the tubular member 10' includes an instrument lumen 18a', an inflation lumen 18c', and a plurality of drainage ports 19b' on the distal end 14' proximal to the balloon 30' that communicate with a drainage lumen 18b'. Alternatively, the drainage lumen 18b' may be omitted and one or more drainage ports may be provided that communicate with the instrument lumen (not shown), e.g., a plurality of perforations in the wall of the tubular member 10' proximal to the balloon 30' that communicate directly with the instrument lumen 18a'.

The catheter 8' (or other embodiments herein) may be constructed in length and/or shape such that the portion of the catheter 8' including the drainage ports 19b' tends to pass through the dependent areas of the pericardial space, e.g., to better remove liquids that may accumulate, e.g., on the posterior aspect of the heart while the outlet 19a' of the instrument lumen 18a' is positioned at the target location for performing intervention or diagnosis. Where air is of greater concern, the catheter 8' may be constructed in length and/or shape such that the drainage ports 19b' tend to pass through the non-dependent areas of the pericardial space, e.g., the anterior wall, while the outlet 19a' of the instrument lumen 18a' is positioned at the target location for diagnosis or treatment.

Figure 4:
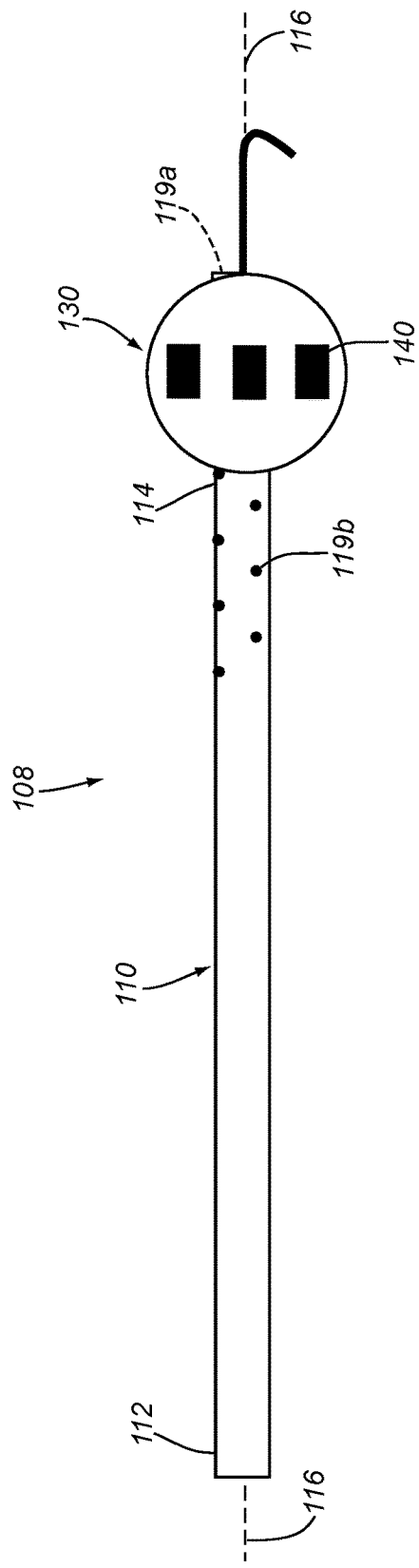
FIG. 4 is a side view of another embodiment of an access and/or ablation catheter.

Turning to FIG. 4, another embodiment of a catheter 108 is shown that generally includes a tubular member 110 including proximal and distal end 112, 114, and a balloon 130 carried on the distal end 114, similar to other embodiments herein. The tubular member 110 includes an instrument lumen (not shown), e.g., extending from the proximal end 112 to an outlet 119a in the distal tip 115, an inflation lumen (also not shown) communicating with the interior of the balloon 130, and a drainage lumen communicating with the drainage ports 119b proximal to the balloon 130. Unlike the previous embodiments, the balloon 130 may include one or more electrodes 140, e.g., a plurality of mapping and/or ablation electrodes carried on an exterior surface of the balloon 130.

Figure 5:
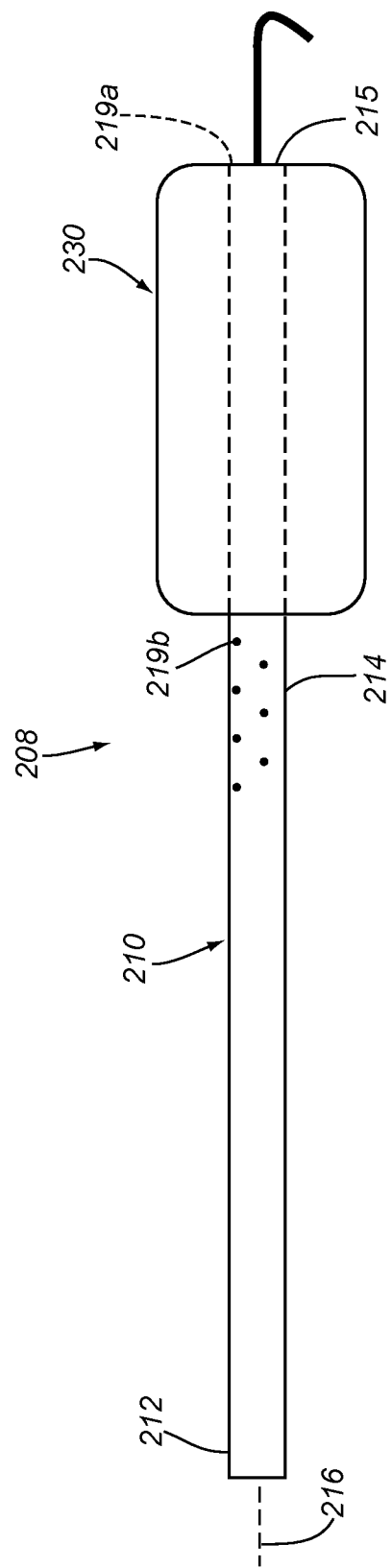
FIG. 5 is a side view of yet another embodiment of an access catheter.

Turning to FIG. 5, yet another embodiment of a catheter 208 is shown that generally includes a tubular member 210 including proximal and distal end 212, 214, and a balloon 230 carried on the distal end 214, generally similar to other embodiments herein. The tubular member 210 includes an instrument lumen (not shown), e.g., extending from the proximal end 212 to an outlet 219a in the distal tip 215, and an inflation lumen (also not shown) communicating with the interior of the balloon 230. Optionally, the tubular member 210 may include a drainage lumen communicating with drainage ports 219b proximal to the balloon 230 and/or an imaging lumen communicating with an imaging assembly on the distal end 214 (not shown). Unlike the previous embodiments, the balloon 130 may have a substantially uniform cylindrical shape when inflated, as shown, or may have an oval or other cross-sectional shape (not shown).

Turning to FIG. 6, an exemplary method is shown for performing a medical procedure within the pericardial space 94, i.e., between a patient's heart 90 and the pericardial sac 92, e.g., using the catheter 8 of FIGS. 1 and 2 (although the methods are equally applicable to other embodiments herein). Initially, the distal end 14 of the catheter 8 may be introduced into the patient's body, e.g., from the patient's skin 96 through the pericardial sac 92 into the pericardial space 94 with the balloon 30 in the contracted condition. For example, the distal end 14 of the catheter 8 may be introduced into the patient's chest, e.g., using minimally invasive or open surgical access. Optionally, a stylet (not shown) may be positioned in the catheter 8 to at least partially straighten the catheter 8 and/or otherwise facilitate advancement of the distal end 14 into the pericardial space 94.

Once the distal end 14 is exposed within the pericardial space 94, the balloon 30 may be expanded, which may open the pericardial space 94 and the catheter 8 may be manipulated to place the balloon 30 against the wall of the heart 90. During manipulation, the imaging assembly 40 may be used to acquire images of the pericardial space 94 and heart 90. In addition, external imaging may be used, if desired in conjunction with acquiring images using the imaging assembly 40. The catheter 10 may be manipulated further as desired, e.g., to move the distal end 14 along the wall of the heart 90 until a target location is identified for treatment. For example, a target location 98 may be identified in the images and/or by electrical mapping (e.g., using electrodes on the balloon, e.g., as shown in FIG. 4) for performing an ablation procedure, whereupon a distal end 84 of an ablation probe 80 may be introduced through the instrument lumen 18a and out the outlet 19a (as best seen in FIG. 2A) and placed against the target location 98. One or more electrodes or other sources of energy delivery (e.g., cryo energy, laser energy, RF energy, ultrasound energy, high voltage energy, etc.) 86 on the distal end 84 may be activated, as desired, to ablate tissue at the target location 98 with the balloon 30 also serving to direct the pericardium 92 to avoid ablating unintended structures. Additionally, fluid may be introduced at or around the point of energy delivery, e.g., via a lumen (not shown) of the ablation probe 80 and/or via the catheter 8 (e.g., via the instrument lumen 18a or a dedicated lumen), e.g., to cool, provide a conductive pathway, and/or otherwise modulate delivery of energy to the target ablation site. The ablation probe 80 and/or catheter 8 may be further manipulated, as desired to treat additional locations of the heart 90.

At any time during the introduction, manipulation, and/or ablation, fluid may be infused and/or aspirated via the drainage ports 19b. For example, contrast may be infused via the ports 19b to facilitate imaging the region, and/or fluid may be removed, e.g., contrast, bodily fluids, and/or air entrained through the catheter 8 and/or access site. In this manner, excess fluid within the pericardial space 94 may be removed as desired, e.g. to avoid fluid building up and compressing the heart 90, which may otherwise impair heart function, lead to tamponade, and/or increase defibrillation thresholds, and the like.

Removal of fluid may be intermittent or continuous. As one example, the operating clinician may intermittently aspirate fluid, e.g., using a syringe (not shown) coupled to the side port 52b (shown in FIG. 2). Alternatively a vacuum pump or other source of suction may be attached to the side port 52a of the catheter 8, e.g., to aspirate fluid via the drainage ports 19b. Furthermore, substantially continuous suction may be applied to the drainage ports 19b, e.g., to ensure that minimal air, contrast, saline, blood, and/or other fluid accumulates in the pericardial space during the procedure.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system for performing a procedure within a region of a patient's body, comprising:
    an access catheter comprising a tubular member including a proximal end, a distal end sized for introduction into a patient's body and terminating in a distal tip, the distal end carrying an imaging assembly within a balloon oriented for imaging distally beyond the balloon, an instrument lumen extending from the proximal end to an outlet in the distal tip beyond the balloon, and a drainage lumen extending from the proximal end to one or more ports on the distal end of the tubular member outside and proximal to the balloon, wherein the drainage lumen terminates before the distal tip of the tubular member;
    an ablation probe comprising a proximal end, a distal end sized for introduction through the instrument lumen and out the outlet distally beyond the distal tip, and one or more ablation elements on the distal end for delivering energy to tissue; and
    a source of fluid coupled to one of the access catheter and the ablation probe for delivering fluid through a lumen to modulate energy delivered by the one or more ablation elements to tissue.

2. The system of claim 1, further comprising a source of vacuum coupled to the access catheter proximal and communicating with the drainage lumen for aspirating fluid from a region adjacent the access catheter distal end via the one or more ports.

3. The system of claim 2, wherein the source of vacuum comprises one of a syringe and a vacuum pump.

4. The system of claim 1, wherein the source of fluid comprises one of a syringe or a pump coupled to the access catheter proximal end and communicating with the drainage lumen for delivering fluid from the syringe or pump through the one or more ports to a region adjacent the access catheter distal end.

5. The system of claim 1, wherein the source of fluid comprises one of a syringe or a pump coupled to the access catheter proximal end and communicating with the instrument lumen for delivering fluid from the syringe or pump through the instrument lumen around the ablation probe to a region adjacent the access catheter distal end.

6. The system of claim 4, wherein the syringe or pump is configured to selectively deliver fluid and aspirate fluid from the region adjacent the access catheter distal end via the one or more ports.

7. The system of claim 1, wherein the source of fluid comprises a syringe or pump coupled to the ablation probe proximal end and communicating with an infusion lumen for delivering fluid from the syringe through one or more outlets on the ablation probe distal end to a region adjacent the access catheter distal end.

8. The system of claim 1, wherein the balloon is expandable from a contracted condition to an enlarged condition, and wherein the balloon has a non-circular cross-section in the enlarged condition.

9. The system of claim 8, wherein the balloon has an ovular or elliptical cross-section in the enlarged condition.

10. The system of claim 1, wherein the balloon carries one or more mapping or ablation electrodes.

11. The system of claim 1, wherein the tubular body comprises one or more pull wires for steering or deflecting the distal end.

12. An apparatus for accessing a region within a patient's body, comprising:
   a tubular member comprising a proximal end, a distal end sized for introduction into a patient's body, and one or more lumens extending between the proximal and distal ends;
   an imaging assembly on the distal end; and
   a substantially transparent expandable member attached to the tubular member distal end such the imaging assembly is disposed within an interior of the expandable member, the imaging assembly imaging oriented for imaging distally through a surface of the expandable member,
   wherein the tubular member further comprises a drainage lumen extending from a proximal port on the tubular member proximal end to one or more drainage ports on the tubular member distal end outside and proximal to the expandable member.

13. The apparatus of claim 12, wherein the expandable member is expandable from a contracted condition to an enlarged condition when fluid is introduced through an inflation lumen of the tubular member into the interior of the expandable member.

14. The apparatus of claim 13, wherein the expandable member has a non-circular cross-section in the enlarged condition.

15. The apparatus of claim 14, wherein the expandable member has an ovular or elliptical cross-section in the enlarged condition.

16. The apparatus of claim 12, further comprising a source of vacuum coupled to the tubular member proximal and communicating with the drainage lumen for aspirating fluid from a region adjacent the tubular member distal end via the one or more ports.

17. The apparatus of claim 16, wherein the source of vacuum comprises one of a syringe and a vacuum pump.

18. The apparatus of claim 12, further comprising a source of fluid coupled to the tubular member proximal end and communicating with the drainage lumen for delivering fluid from the source through the one or more ports to a region adjacent the access catheter distal end.

19. The apparatus of claim 18, wherein the source of fluid comprises one of a syringe or a pump.

20. The apparatus of claim 12, wherein the expandable member comprises a balloon carrying one or more mapping or ablation electrodes.

21. A method for performing a procedure within a pericardial space adjacent a patient's heart and pericardium, comprising:
   introducing a distal end of a catheter into the pericardial space adjacent the patient's heart such that an expandable member and one or more drainage ports on the distal end are located within the pericardial space;
   expanding the expandable member within the pericardial space to separate the pericardium from the patient's heart;
   imaging tissue within the pericardial space to identify a target location of the patient's heart;
   introducing a medical device through the catheter and out the distal end into the pericardial space;
   performing a procedure at the target location using the medical device; and
   draining fluid from the pericardial space via the one or more drainage ports.

22. The method of claim 21, wherein the medical device comprises an ablation probe, and wherein performing a procedure comprises delivering energy from the ablation probe to tissue at the target location.

23. The method of claim 22, further comprising delivering fluid into the pericardial space to modulate the energy delivered from the ablation probe.

24. The method of claim 23, wherein fluid is drained to prevent the delivered fluid from accumulating within the pericardial space.

25. The method of claim 23, wherein the fluid is delivered into the pericardial space via the one or more drainage ports.

* * * * *